United States Patent [19]

Bergersen

[11] 4,139,944
[45] Feb. 20, 1979

[54] ORTHODONTIC APPLIANCE AND METHOD OF USING SAME DURING MIXED DENTITION STAGE

[76] Inventor: Earl O. Bergersen, 950 Linden Ave., Winnetka, Ill. 60093

[21] Appl. No.: 748,873

[22] Filed: Dec. 9, 1976

Related U.S. Application Data

[63] Continuation-in-part of Ser. No. 626,267, Oct. 28, 1975, abandoned.

[51] Int. Cl.² .................................................. A61C 7/00
[52] U.S. Cl. ....................................................... 32/14 D
[58] Field of Search ......................................... 32/14 D

[56] References Cited
U.S. PATENT DOCUMENTS

| | | | |
|---|---|---|---|
| 2,789,351 | 4/1957 | Gordon | 32/14 B |
| 3,178,820 | 4/1965 | Kesling | 32/14 C |
| 3,457,916 | 7/1969 | Wolicki | 32/14 C |
| 3,478,429 | 11/1969 | Shilliday | 32/14 C |

*Primary Examiner*—Robert Peshock
*Attorney, Agent, or Firm*—Larson, Taylor and Hinds

[57] ABSTRACT

A method and an orthodontic positioner for preventing or correcting overbite and/or overjet at a mixed dentition stage wherein a patient has permanent incisors and lost, unreplaced canine and deciduous molar teeth. A positioner essentially of a size for a person having incisors the same size as that of the patient but with a full set of permanent teeth (posteriorly to the permanent canine) is trimmed back posteriorly and along the gingival margins to fit in the patient's mouth without abrading the labial-buccal gum surfaces. This will concurrently provide depression of the incisors and guidance of eruption of the permanent canine and bicuspid teeth.

36 Claims, 9 Drawing Figures

ORTHODONTIC APPLIANCE AND METHOD OF USING SAME DURING MIXED DENTITION STAGE

This application is a continuation-in-part of my earlier application Ser. No. 626,267 filed Oct. 28, 1975 and is now abandoned.

BACKGROUND OF THE INVENTION

This invention relates to tooth positioning appliances, and in particular it relates to the early treatment of overbite and overjet problems.

In the field of orthodontics, at the point in time at which all of the deciduous teeth have been replaced by permanent teeth, conventional orthodontic devices such as bands or the like are often used for straightening teeth to bring them to a predetermined position of proper or close to proper occlusion. To bring teeth into a final position of desired orientation in the mouth, the orthodontists will often use a tooth positioner, an example of which is shown in my earlier U.S. Pat. No. 3,898,736. The said patent relates to a preformed tooth positioner. However, custom-made positioners of this general type have also been known for many years, as illustrated for example in the Kesling U.S. Pat. No. 2,467,432.

A basic problem with these and other current orthodontic practices and equipment is that treatment does not commence until the stage is reached at which all deciduous teeth have been replaced by their corresponding permanent teeth, and this is so notwithstanding the fact that many real or potential orthodontic problems are recognizable at much earlier times, for example upon eruption of the first permanent incisor teeth. A particular problem which can be recognized at such an early stage is overbite and/or overjet.

Thus, it would solve a basic problem in the field of orthodontics and provide a significant advance therein to provide procedures and equipment for commencing treatment of orthodontic problems during the mixed dentition stage which precedes that stage at which all deciduous teeth have been replaced.

SUMMARY OF THE INVENTION

Thus, it is a purpose of the present invention to overcome the above noted shortcomings in the field of orthodontics by providing a method and apparatus for treating orthodontic problems during the patient's mixed dentition stage.

This purpose of the present invention is achieved by redesigning and utilizing in a new way an orthodontic positioner of the type which is U-shaped in plan view and includes at least an upper or lower but normally both upper and lower troughs including tooth receiving depressions for receiving, retaining and repositioning the teeth received therein.

The present invention is based on my realization that there exists, at a certain early stage in a child's orthodontic development, a situation susceptible to effective treatment. Specifically, at an early age such as from 6 to 8 or 9 all of a child's permanent incisor teeth have fully erupted, after which a subsequent stage is reached at approximately ages 10 through 12 during which the child loses the deciduous canine and the first and second deciduous molars, these teeth being ultimately replaced, respectively, by the permanent canine, the permanent first bicuspid and the permanent second bicuspid. This said subsequent stage occurs at a time when the child also has in its mouth a permanent first molar (which erupts at about age 6, and hence they name "six year molar"). During this said subsequent stage, i.e. when the child has lost either the first or both of the deciduous molars and has erupted permanent incisors and a permanent first (six year) molar, which will be referred hereinafter as the "subject stage", certain problems are clearly discernable, and of particular interest in this regard are problems of overbite and overjet.

In accordance with the present invention, an orthodontic positioner of the type referred to above can be used in selective cases to correct such overbite and overjet. The result of this development is that a potential orthodontic problem is prevented from developing and converted into a perfect functional dentition. Basically, the concept is to use a positioner of the type described for depressing the incisor teeth while concurrently guiding the permanent bicuspids and permanent canine teeth to their proper positions and controlling their vertical level of eruption. This technique has the significant advantage that the situation can be perfected prior to the establishment of the interseptal periodontal fibers and permanently control the vertical level of the permanent teeth so that a difficult overbite problem in the permanent dentition is prevented from occurring.

This technique is particularly adaptable to selective cases. There should be no potential mandibular or maxillary crowding, especially of the incisor teeth since such crowding constitutes a more serious problem which would require braces. Further, the situation is best adaptable to a Class I or an end-to-end relationship of the first permanent molars but would probably be inapplicable to a Class II relationship. A Class I relationship means that the upper first permanent molar is at least one half tooth width rearwardly of the corresponding lower first permanent molar. End-to-end of course means that the maxillary first permanent molars are directly above their corresponding first mandibular permanent molars. However, a class II relationship means that the maxillary first permanent molar is at least one half tooth width forward of its corresponding first permanent mandibular molar, meaning that there will be crowding of the anterior maxillary teeth to an extent which would require braces. Further, this technique can treat any degree of vertical overbite but preferably the horizontal overjet should be no greater than 3 to 4 millimeters.

The orthodontic positioner is basically of the type described in my said earlier patent. However, to be functional in the present situation, the gingival edges of the labial-buccal flange of the positioner must be considerably cut back. The reason for this is not only that the younger child has a smaller mouth than the mouth of a patient for which a positioner of that type would generally be utilized, but also because the bone structure of the younger child is different. Specifically, the labial-buccal sides of the gum protrude bucally a greater extent proportionally than would be the case for the same person having only permanent teeth since at the early stage prior to eruption of the posterior permanent teeth, such teeth are located down in the gum and not necessarily on the center line of the teeth, but rather slightly bucally of center. Hence, in redesigning a positioner for use by a child in the mixed dentition stage having only permanent incisors and a permanent first molar, said cutting back of the positioner avoids abrading the labial-buccal gum surfaces. The lingual flange is already cut back considerably so that it is not necessary to further cut back this flange; and in any event there is not the same problem of protruding bone structure on the lingual side as exists on the labial-buccal side. In addition, since a positioner of this type is normally designed for receiving the teeth of a twelve year old child, the dentition of which includes a second permanent molar (which erupts at approximately age 12 and hence the name, "twelve year molar"), and since the subject patient in the present case is younger than this, then the rear portion of the positioner adapted to receive the second permanent molar can also be trimmed off.

Since the redesigned positioner of the present invention includes tooth receiving depressions for teeth which do not even exist, namely the permanent canine and bicuspid teeth, the present invention is particularly adapted for using a preformed positioner wherein such depressions already exist. The other type of positioner, the custom-made positioner would be inapplicable because the depresssions therein are based on impressions of existing teeth and do not normally include estimates as to the size and shape of non-existing teeth. Of course one could possibly make a custom positioner and guess as to the size and shape of the non-existent permanent canine and bicuspid teeth, and if such guesswork were accurate, the present invention might possibly be adaptable for use with a custom positioner as well as a preformed positioner.

As noted above, the mixed dentition stage also includes that earlier point in time when the child's permanent incisors and permanent first molars have erupted and the child has lost its deciduous canine teeth, its deciduous first molars, but the child has not lost its deciduous second molars. When the present invention is used at this earlier stage, the positioner will differ from that described above for the case where both deciduous molars have been lost. In this case wherein the second deciduous molars are still present, the depressions for the permanent second bicuspids, upper and lower, left and right, will each be replaced by a depression shaped and sized to receive the second deciduous molar. The lower second deciduous molars are about 2 mm wider than the lower permanent second bicuspids and the upper second deciduous molars are about 1 mm wider than the upper permanent second bicuspids, said dimensions taken in the mesio-distal (front to back) direction. The depressions for the first permanent molars must also be placed further back by that amount. In addition, there must be no interproximal projections between the depressions for the first permanent molars and the adjacent second deciduous molars so that when the second deciduous molars are lost and the smaller second permanent bicuspids erupt into the mouth, the first permanent molars can then drift forward to close up the extra space.

Thus, it is an object of the present invention to provide for the treatment of orthodontic problems at a point in time much earlier than the conventional commencement point for orthodontic treatment, and in particular for providing treatment during the mixed dentition stage.

It is another object of this invention to provide a new and improved method and device for early treatment of overjet and overbite problems.

It is still another object of this invention to provide an orthodontic method and device for controlling overbite and/or overjet by causing depression of the permanent incisor teeth while guiding and controlling vertical eruption of the permanent canine and bicuspid teeth.

It is still another object of this invention to provide an orthodontic positioner which is redesigned relative to a conventional orthodontic positioner, especially by trimming back the gingival margins of the labial-buccal flange, for fitting the mouth of a younger child whose teeth are at the mixed dentition stage, especially to avoid abrading the tissues of the labial-buccal gum surfaces.

These and other objects and advantages of the present invention will become apparent from the detailed description to follow, together with the accompanying drawings.

BRIEF DESCRIPTION OF THE DRAWINGS

There follows a detailed description of a preferred embodiment of the invention to be read together with the accompanying drawings in which.

DETAILED DESCRIPTION OF THE PREFERRED EMBODIMENT

Figure 1:
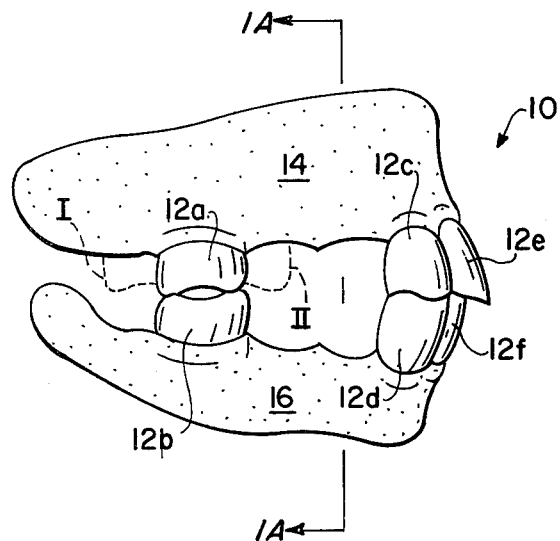
FIG. 1 is a side elevational fragmentary view of a human mouth at one type of mixed dentition stage and including maloccluded teeth in need of orthodontic treatment.

Referring now to the drawings, like elements are represented by like numerals throughout the several views.

FIG. 1 is a view of the mouth 10 of a child at a type of mixed dentition stage having permanent first molars 12a and 12b and permanent incisors, the right upper and lower lateral incisors 12c and 12d and the right center upper and lower incisors 12e and 12f being shown in the figures. The space between the illustrated teeth is the area wherein deciduous canine and molars have been lost but not yet replaced by their corresponding permanent canine, first bicuspid and second bicuspid teeth. As is evident in FIG. 1, the permanent incisors illustrate a potential overbite and overjet problem, i.e. overbite meaning the vertical projection of the upper incisors below the plane of the top of the lower incisors and overjet meaning the horizontal distance between the occlusal edges of the corresponding upper and lower incisors 12e and 12f. In this case the permanent molars 12a and 12b abut each other in what is referred to as end-to-end relationship. The most desirable case is that referred to as class I wherein the upper molar 12a is located rearwardly of the lower molar 12b by one half tooth width or more as represented by the dotted line I in FIG. 1. That case is preferable because it leaves the most room anteriorly thereof for the incoming and existing permanent teeth. The end-to-end relationship is satisfactory in that it still leaves sufficient room for the incoming teeth such that it is still possible to treat this type of mouth with the positioner in accordance with the present invention. This would not be the case, however, with a class II situation wherein the upper molar 12a is located forwardly of the lower molar 12b to the position represented by dotted line II.

Before discussing the application of the present invention for treating the mouth 10, reference is made to FIGS. 2 through 5 for a discussion of the structure and operation of the conventional preformed positioner as discussed in my said earlier patent.

Figure 2:
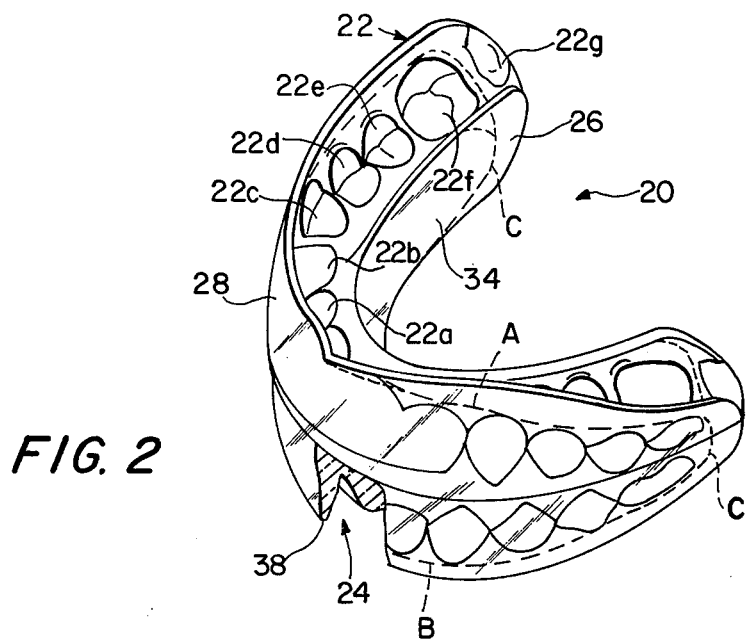
FIG. 2 is a perspective view showing generally the upper surface of a tooth positioner with a portion cut away to reveal a section of the lower surface thereof.
Figure 6:
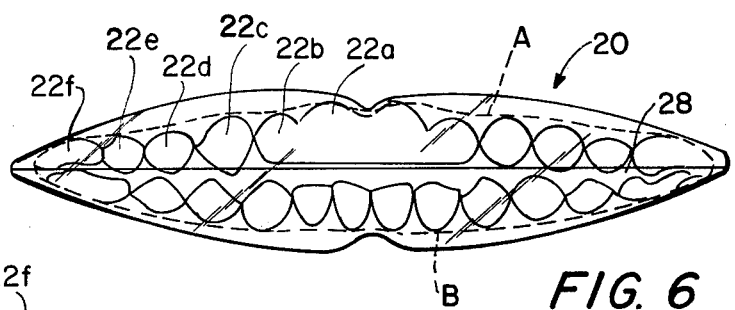
FIG. 6 is a front elevational development view of FIG. 2 but on a reduced scale.

Referring to FIGS. 2 through 5, and disregarding for the moment the dotted lines shown therein, these figures illustrate the conventional orthodontic positioner. After the child has all of its permanent teeth back to the second molar, conventional orthodontic devices such as bands or the like are normally utilized for initial straightening of the teeth in the mouth to bring the teeth into a predetermined position of proper or close to proper occlusion. The positioner is then utilized to bring the teeth into a final desired position. Such a retainer 20, as shown in FIG. 2, is generally U-shaped in plan so as to conform to typical human mouth configuration and generally H-shaped in cross-section, providing an upper or superior tooth receiving trough 22 and a lower or inferior tooth receiving trough 24. The sides of the troughs 22 and 24 are bounded by lingual flange 26 which covers the rear of the teeth of the upper and lower arch and a labial-buccal flange 28 which cover the front of the teeth of both arches.

Both the upper and lower tooth receiving surfaces 22 and 24 are provided with a plurality of tooth receiving depressions or sockets, such as 22a, 22b, 22c, 22d, 22e, and 22f, of different configurations for receiving the different permanent teeth of the mouth from the central incisors through the cuspids and bicuspids, into the first molar, and half of the second molar area. Alternatively, the positioner can of course be made having only an upper trough 22 or only a lower trough 24.

Figure 3:
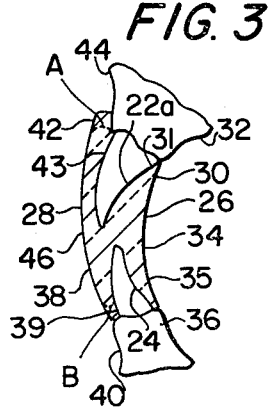
FIG. 3 is a fragmentary section view through a human mouth in the area of the central incisors and showing the tooth positioner of FIG. 2 in place therein.
Figure 4:
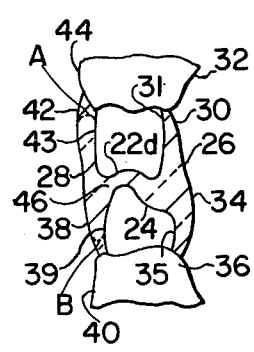
FIG. 4 is a fragmentary section view through the human mouth in the area of the permanent bicuspid teeth and showing the tooth positioner of FIG. 2 in place therein.
Figure 5:
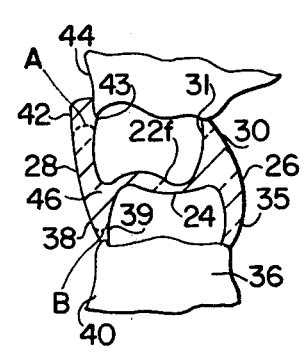
FIG. 5 is a fragmentary section view of the human mouth in the molar area showing the tooth positioner of FIG. 2 in place therein.

As best seen in FIGS. 3 through 5, the upper lingual flange 30, which secures the lingual cingulum areas of the upper anterior teeth and lingual surfaces of the lingual cusps of the upper posterior teeth, includes an inwardly directed rib 31 and covers a portion of the upper lingual gingival area 32, and the lower lingual flange 34 generally embraces the cingulum area of the lower anterior teeth and the lingual surface of the lingual cusps of the lower posterior teeth and includes an inwardly directed rib 35. This flange also extends over a portion of the lower lingual gingival tissue 36. The lower labial and buccal flange 38 which covers the labial and buccal surfaces of the lower anterior and posterior teeth includes an inwardly directed rib 39 and also extends over a portion of the lower labial and buccal gingival tissue 40 and the upper labial and buccal flange 42 has an inwardly directed rib 43 and covers the entire labial and buccal surfaces of the upper anterior and posterior teeth and also embraces a small portion of the upper gingival tissue 44.

The various pockets (such as 22a and 22b) in the positioner for the upper and lower teeth are made so that the teeth are snugly embraced thereby. The isthmus 46 which joins the lingual and buccal or labial halves of the positioner is generally thin, though it differs in dimension between the posterior region and anterior region so as to resemble the normal relaxed clearance between the teeth with the exception that the isthmus is slightly thinner in the posterior region. This enables all the occlusal and incisal surfaces of the teeth to be in contact with the positioner at the same time when occlusal pressure is applied. Alternatively however, the thickness of the isthmus can be varied to be increased in one of the anterior or posterior regions relative to other of said regions to cause either the anterior or posterior teeth to contact the isthmus before the other to correct for overbite or open bite, respectively, as described in my copending application Ser. No. 543,356, filed Jan. 23, 1975.

It has also been found that a preformed positioner of this type can include metal clasps imbedded in the rear portion thereof, as shown in U.S. Pat. Nos. 3,178,820 and 3,837,081, to more firmly secure the positioner in place in the patient's mouth.

It has further been discovered that it is desirable to make the tooth positioner out of a semi-resilient plastic transparent material. The transparency enables the dental practitioner to actually see where the tooth movement will take place by observing blanching of tissue around the teeth and also enables him to detect potential soft tissue sore spots due to abnormal impingement of the flanges of the tooth positioner.

Figure 1A:
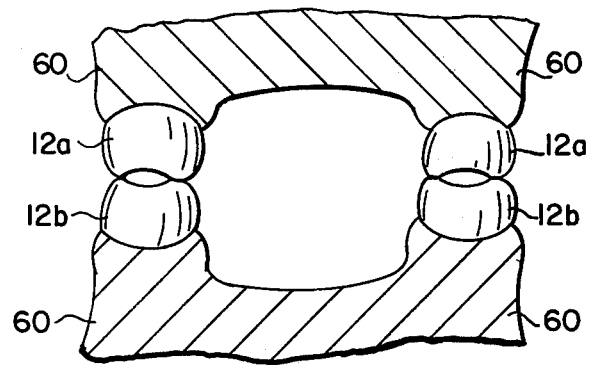
FIG. 1A is a cross-sectional view taken along line 1A—1A of FIG. 1.

Referring again to FIG. 1, and also to FIG. 1A, as noted above, the present invention seeks to provide a method and an apparatus for orthodontic treatment of teeth at an earlier than usual stage, namely the mixed dentition stage as described above with respect to FIG. 1. This is accomplished by providing an orthodontic positioner so constructed and arranged that the permanent incisor teeth 12c, 12d, 12e, and 12f will be depressed while the space between the incisors and the first permanent molar will be given vertical clearance to guide and control eruption of the permanent canine and bicuspid teeth.

FIG. 1A illustrates a particular problem which exists in the mouth of a child at the mixed dentition stage. As is evident therein, the buccal gum tissues protrude significantly outwardly as represented at areas 60. The reason for this protrusion is that the not yet erupted permanent canine and bicuspid teeth are located bucally of the illustrated first molars. Hence, a conventional orthodontic positioner designed for a person having incisor teeth of the size as shown in FIG. 1 would not be operable for performing the above described function in a mouth at the mixed dentition stage as illustrated in FIGS. 1 and 1A. The main reason for this is that the outer margins of the labial-buccal flange of such a positioner would abrade the protruding labial-buccal gum surfaces, irritating the same, for example at the areas 60 of FIG. 1A. In addition, it is at least desirable if not absolutely necessary to trim back the portion of the conventional positioner provided for the second molar since there is no second molar in a child patient at the said mixed dentition stage.

Referring now to FIGS. 2 through 6, there is illustrated thereon in dotted lines the portions of the conventional positioner which would have to be trimmed back in order to provide a positioner operable for treating a child patient at said mixed dentition stage. Referring to these figures, the labial-buccal flange is trimmed back along the upper portion thereof at line A, along the lower portion thereof at line B, and at the posterior end thereof to eliminate depression 22g of the second molar at line C. Except for this trimming back, it will be understood that the positioner will retain all of the structure and attendant advantages of the previously described preformed positioner.

Figure 7:
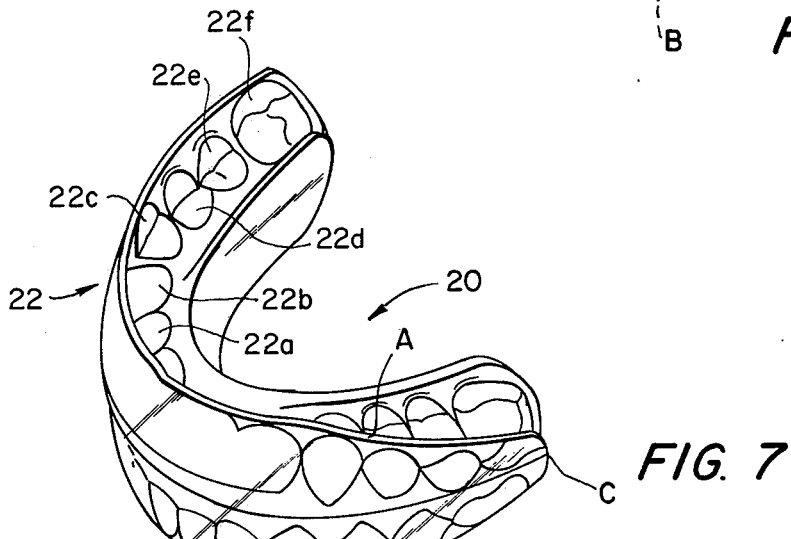
FIG. 7 is a perspective view similar to FIG. 2 but wherein the positioner has been appropriately trimmed in accordance with the present invention.
Figure 8:
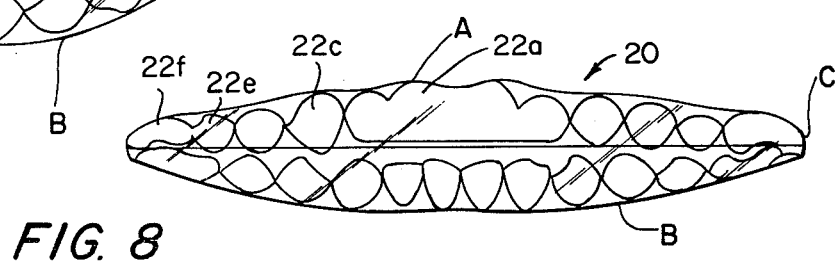
FIG. 8 is a front elevational development of FIG. 7 but on a reduced scale.

FIGS. 7 and 8 illustrate the final trimmed back positioner ready for use in a patient at the mixed dentition stage.

In the case of treatment at the earlier point in time when the child still has its second deciduous molars, the depressions 22e (top and bottom, both sides) would be altered as described earlier to fit the child's second deciduous molars rather than the permanent second bicuspids, and any interproximal projections between those depressions 22e and adjacent depressions 22f for the first permanent molars would be eliminated.

Although the specific extent of the trimming back may depend on many different factors, it has been found that the trim line A along the upper gingival edge of the labial-buccal flange should be such as to take off approximately 50 to 70 percent of the margin between the gum line and the outer margin of the labial-buccal flange in the region of the anterior teeth and approximately 70 to 90 percent of said distance between the gum line and the outer margin toward the upper posterior teeth. The corresponding percentages for the lower trim line B would be approximately 70 to 90 percent in the region of the anterior teeth and approximately 110 to 120 percent in the area of the posterior teeth, i.e. at the posterior lower teeth it may be necessary to trim back the edge even occlusally of the gum line. The amount trimmed back can also be measured in terms of specific dimensions outwardly (i.e. gingivally) from the occlusal edges of the teeth. Such dimensions are given by way of a preferred embodiment in the following Table I which gives these dimensions as applied to an entire set of preformed positioners currently sold under the Registered Trademark Ortho-tain and which are designed to fit essentially the entire dental patient population. Hence, the set of positioners dimensioned as in Table I, provides a set of positioners adapted to fit a large percentage of the applicable dental patient population at said subject mixed dentition stage. The explanations of the columns of parts 1–4 of Table I are set forth in part 5 of Table I and the sizes of the positioners in Table I correspond to those sold under the said Registered Trademark Ortho-tain, and as described in my said U.S. Pat. No. 3,898,736.

In addition to Table I, Table II gives variations for Table I in the case referred to above of treating a child who still has its second deciduous molars.

Table III provides a variation of the amount by which the gingival edges are trimmed back in order to prevent damage to higher gums on young children.

Although these Tables are applicable only to the non-extraction situation, the invention is also applicable to serial-extraction cases wherein the first permanent bicuspids (upper and lower) are extracted prior to their eruption in the mouth. In this case the positioner design would be similar to the non-extraction positioner of Table I with the single exception that the depressions for the first permanent bicuspids would not be present, and all else would remain essentially the same.

Table I (part 1)

Gross Dimensions Of Preformed Eruption Guidance Appliance In MM.

| size | a | b | c | d | e | f | g | h | i | j |
|---|---|---|---|---|---|---|---|---|---|---|
| 1 G | 16.5 | 12.0 | 9.0 | 14.6 | 35.4 | 53.2 | 22.5 | 14.0 | 13.4 | 12.9 |
| 1¼ G | 16.8 | 12.3 | 9.2 | 14.9 | 36.4 | 54.2 | 23.2 | 14.1 | 13.7 | 13.0 |
| 2 G | 17.0 | 12.6 | 9.3 | 15.2 | 37.5 | 55.1 | 24.0 | 14.3 | 13.9 | 13.1 |
| 2¼ G | 17.3 | 12.8 | 9.5 | 15.5 | 38.5 | 56.1 | 24.7 | 14.4 | 14.2 | 13.2 |
| 3 G | 17.6 | 13.1 | 9.7 | 15.8 | 39.6 | 57.0 | 25.4 | 14.6 | 14.5 | 13.2 |
| 3¼ G | 17.9 | 13.4 | 9.8 | 16.1 | 40.6 | 58.0 | 26.1 | 14.7 | 14.7 | 13.4 |
| 4 G | 18.2 | 13.7 | 10.0 | 16.5 | 41.6 | 59.0 | 26.9 | 14.9 | 15.0 | 13.6 |
| 4¼ G | 18.5 | 14.0 | 10.2 | 16.8 | 42.7 | 60.0 | 27.6 | 15.0 | 15.3 | 13.7 |
| 5 G | 18.7 | 14.2 | 10.4 | 17.1 | 43.7 | 60.9 | 28.3 | 15.2 | 15.6 | 13.8 |
| 5¼ G | 19.0 | 14.5 | 10.5 | 17.4 | 44.8 | 61.8 | 29.1 | 15.3 | 15.8 | 13.9 |
| 6 G | 19.3 | 14.8 | 10.7 | 17.7 | 45.8 | 62.8 | 30.8 | 15.5 | 16.1 | 14.0 |

Table I (part 2)

Gross Dimensions of Preformed Eruption Guidance Appliance In MM.

| size | k | l | m | n | o | p | q | r | s | t | u |
|---|---|---|---|---|---|---|---|---|---|---|---|
| G | 8.8 | 8.7 | 2.5 | 7.3 | 5.9 | 7.1 | 6.1 | 4.3 | 2.2 | 3.3 | 9.0 |
| 1¼ G | 9.1 | 8.7 | 2.5 | 7.5 | 6.0 | 7.2 | 6.1 | 4.3 | 2.4 | 3.3 | 9.2 |
| 2 G | 9.3 | 8.7 | 2.5 | 7.6 | 6.1 | 7.3 | 6.2 | 4.3 | 2.5 | 3.3 | 9.4 |
| 2¼ G | 9.6 | 8.7 | 2.5 | 7.7 | 6.3 | 7.4 | 6.2 | 4.3 | 2.7 | 3.3 | 9.6 |
| 3 G | 9.9 | 8.7 | 2.5 | 7.9 | 6.4 | 7.5 | 6.3 | 4.3 | 2.9 | 3.3 | 9.8 |
| 3¼ G | 10.1 | 8.7 | 2.5 | 8.0 | 6.6 | 7.6 | 6.3 | 4.3 | 3.0 | 3.3 | 10.0 |
| 4 G | 10.4 | 8.7 | 2.5 | 8.2 | 6.7 | 7.7 | 6.4 | 4.3 | 3.2 | 3.3 | 10.2 |
| 4¼ G | 10.7 | 8.7 | 2.5 | 8.4 | 6.8 | 7.8 | 6.4 | 4.3 | 3.4 | 3.3 | 10.4 |
| 5 G | 11.0 | 8.7 | 2.5 | 8.5 | 6.9 | 7.9 | 6.5 | 4.3 | 3.6 | 3.3 | 10.6 |
| 5¼ G | 11.2 | 8.7 | 2.5 | 8.6 | 7.1 | 8.0 | 6.5 | 4.3 | 3.7 | 3.3 | 10.8 |
| 6 G | 11.5 | 8.7 | 2.5 | 8.8 | 7.2 | 8.1 | 6.6 | 4.3 | 3.9 | 3.3 | 11.0 |

Table I (part 3)

Gross Dimensions of Preformed Eruption Guidance Appliance in MM.

| size | aa | bb | cc | d tot. | dd | ee | ff | a tot. | gg | hh | ii | vv tot. | jj | kk | ll | ww tot. |
|---|---|---|---|---|---|---|---|---|---|---|---|---|---|---|---|---|
| 1 G | 6.2 | 5.1 | 3.3 | 14.6 | 7.3 | 5.9 | 3.3 | 16.5 | 6.8 | 5.9 | 3.3 | 16.0 | 7.1 | 6.1 | 1.8 | 16.0 |
| 1¼ G | 6.4 | 5.2 | 3.3 | 14.9 | 7.5 | 6.0 | 3.3 | 16.8 | 6.9 | 6.0 | 3.3 | 16.2 | 7.2 | 6.1 | 1.8 | 15.1 |
| 2 G | 6.6 | 5.3 | 3.3 | 15.2 | 7.6 | 6.1 | 3.3 | 17.0 | 7.1 | 6.1 | 3.3 | 16.5 | 7.3 | 6.2 | 1.8 | 16.3 |
| 2¼ G | 6.8 | 5.4 | 3.3 | 15.5 | 7.7 | 6.3 | 3.3 | 17.3 | 7.1 | 6.3 | 3.3 | 16.7 | 7.4 | 6.2 | 1.8 | 16. |
| 3 G | 7.0 | 5.5 | 3.3 | 15.8 | 7.9 | 6.4 | 3.3 | 17.6 | 7.2 | 6.4 | 3.3 | 16.9 | 7.5 | 6.3 | 1.8 | 16.6 |
| 3¼ G | 7.3 | 5.5 | 3.3 | 16.1 | 8.0 | 6.6 | 3.3 | 17.9 | 7.3 | 6.6 | 3.3 | 17.2 | 7.6 | 6.3 | 1.8 | 16.7 |
| 4 G | 7.6 | 5.6 | 3.3 | 16.5 | 8.2 | 6.7 | 3.3 | 18.2 | 7.4 | 6.7 | 3.3 | 17.4 | 7.7 | 6.4 | 1.8 | 15.9 |
| 4¼ G | 7.8 | 5.7 | 3.3 | 16.8 | 8.4 | 6.8 | 3.3 | 18.5 | 7.6 | 6.8 | 3.3 | 17.7 | 7.8 | 6.4 | 1.8 | 16.0 |
| 5 G | 8.0 | 5.8 | 3.3 | 17.1 | 8.5 | 6.9 | 3.3 | 18.7 | 7.7 | 7.0 | 3.3 | 17.9 | 7.9 | 6.5 | 1.8 | 16.2 |
| 5¼ G | 8.2 | 5.9 | 3.3 | 17.4 | 8.6 | 7.1 | 3.3 | 19.0 | 7.8 | 7.1 | 3.3 | 18.2 | 8.0 | 6.5 | 1.8 | 16.8 |

Table I-continued
(part 3)
Gross Dimensions of Preformed Eruption Guidance Appliance in MM.

| size | aa | bb | cc | d tot. | dd | ee | ff | a tot. | gg | hh | ii | vv tot. | jj | kk | ll | ww tot. |
|---|---|---|---|---|---|---|---|---|---|---|---|---|---|---|---|---|
| 6 G | 8.4 | 6.0 | 3.3 | 17.7 | 8.8 | 7.2 | 3.3 | 19.3 | 7.9 | 7.2 | 3.3 | 18.4 | 8.1 | 6.6 | 1.8 | 16.8 |

Table I
(part 4)
Gross Dimensions Of Preformed Eruption Guidance Appliance In MM.

| size | mm | nn | oo | xx tot. | pp | qq | rr | yy tot. | ss | tt | uu | zz tot. |
|---|---|---|---|---|---|---|---|---|---|---|---|---|
| 1 G | 6.3 | 4.9 | 1.8 | 13.0 | 5.6 | 3.8 | 1.6 | 11.0 | 4.3 | 2.2 | 2.5 | 9.0 |
| 1¼ G | 6.3 | 5.0 | 1.8 | 13.1 | 5.7 | 3.9 | 1.6 | 11.2 | 4.3 | 2.4 | 2.5 | 9.2 |
| 2 G | 6.4 | 5.1 | 1.8 | 13.3 | 5.7 | 4.0 | 1.6 | 11.3 | 4.3 | 2.5 | 2.5 | 9.3 |
| 2¼ G | 6.5 | 5.1 | 1.8 | 13.4 | 5.8 | 4.1 | 1.6 | 11.5 | 4.3 | 2.7 | 2.5 | 9.5 |
| 3 G | 6.6 | 5.2 | 1.8 | 13.6 | 5.9 | 4.2 | 1.6 | 11.7 | 4.3 | 2.9 | 2.5 | 9.7 |
| 3¼ G | 6.6 | 5.3 | 1.8 | 13.7 | 5.9 | 4.3 | 1.6 | 11.8 | 4.3 | 3.0 | 2.5 | 9.8 |
| 4 G | 6.7 | 5.4 | 1.8 | 13.9 | 6.0 | 4.4 | 1.6 | 12.0 | 4.3 | 3.2 | 2.5 | 10.0 |
| 4¼ G | 6.8 | 5.5 | 1.8 | 14.1 | 6.1 | 4.4 | 1.6 | 12.1 | 4.3 | 3.4 | 2.5 | 10.2 |
| 5 G | 6.9 | 5.6 | 1.8 | 14.3 | 6.2 | 4.5 | 1.6 | 12.3 | 4.3 | 3.6 | 2.5 | 10.4 |
| 5¼ G | 6.9 | 5.7 | 1.8 | 14.4 | 6.2 | 4.6 | 1.6 | 12.4 | 4.3 | 3.7 | 2.5 | 10.5 |
| 6 G | 7.0 | 5.8 | 1.8 | 14.6 | 6.3 | 4.7 | 1.6 | 12.6 | 4.3 | 3.9 | 2.5 | 10.7 |

Table I (part 5)

a. Greatest anterior vertical height (labial flange).
b. Vertical height through first pre-molar area (buccal-flange).
c. Vertical height through the first molar area in line with the center of mesio-bucco cusp of the upper molar (buccal-flange).
d. Vertical height through the midline on the anterior surface (labial flange).
e. Gross length of the appliance through the midline to the line perpendicular to it running tangent across the most posterior extents of the appliance.
f. Greatest width through the molar area.
g. Distance between lingual flanges at level of mesio-lingual cusps of the first permanent molars, (upper).
h. Width through the middle of the first upper molar area.
i. Width through the middle of the upper first pre-molar area.
j. Width through the mesial of the central incisors.
k. Height of the lingual flange at the midline.
l. Height of the lingual flange through the first pre-molar area.
m. Height of the most distal portion of the flange midway between the buccal and lingual cusps of the first molar.
n. Height of the upper flange of the retainer from the incisal edge to the flange in the upper arch.
o. Height of the lower flange from the incisal edge of the lower central incisor to the edge of the margin of the retainer.
p. Height of the upper flange from the tip of the cusp of the upper canine to the margin of the retainer.
q. Height of the lower flange from the tip of the lower cusp of the canine to the margin of the retainer.
r. Height of the upper flange from the tip of the mesial buccal cusp to the edge of the margin of the retainer.
s. Height of the lower flange from the tip of the mesial buccal cusp of the lower first molar to the margin of the retainer.
t. Freeway space at the midline or the distance from the tip of the incisal edge of the upper central incisor to the tip of the incisal edge of the lower central incisor.
u. Height of lingual flange at the level of the center of the upper and lower central incisors or the greatest dimension of the retainer on the lingual at the level of the central incisors.
aa. Height of the upper flange of the retainer at the midline from the incisal edges of the central incisors.
bb. Height of the retainer margin of the lower portion of the retainer from the incisal edges of the lower central incisors to the lower margin of the retainer at the midline.
cc. Freeway space between the central incisors at the midline. cc is equivalent to the dimension t. d total is the same dimension as d.
dd. The height of the upper flange of the retainer as measured from the center of the incisal edge of the upper central incisor.
ee. The height of the lower flange of the retainer as measured from the center portion of the incisal edge of the lower central incisor.
ff. Represents the freeway space between the incisal edges of the upper and lower central incisors. a total is the same as No. a.
gg. The height of the upper flange of the retainer as measured from the center portion of the incisal edge of the upper lateral incisor.
hh. The height of the lower flange of the retainer as measured from the center of the incisal edge of the lower central incisor.
ii. Represents the freeway space as measured from between the incisal edges of the upper and lower lateral incisors. vv total represents the total distance between the upper and lower margins of the retainer at the level of the lateral incisor.
jj. Represents the same as p.
kk. Represents the same as q.
ll. Represents the freeway space as measured between the tips of the cusps of the upper and lower canines. ww total represents the total heigt between the margins of the retainer at the level of the canine.
mm. Represents the height of the margin of the retainer as measured from the tip of the buccal cusp of the upper first bicuspid tooth.
nn. Represents the height of the lower flange of the retainer at the level of the tip of the cusp of the lower first bicuspid. (buccal cusp).
oo. Represents the freeway space at the level of the first bicuspid as measured between the tips of the cusps (buccal) of the upper and lower first bicuspids
pp. Represents the height of the upper flange of the retainer at the level of the upper second bicuspid as measured from the tip of the buccal cusp to the margin.
qq. Represents the height of the lower flange of the retainer as measured from the tip of the buccal cusp of the lower second bicuspid.
rr. Represents the freeway space at the level of the second bicuspid as measured between the tips of the buccal cusps of the upper and lower second bicuspids.
ss. Represents same as r.
tt. Represents same as s.

uu. Represents same as m.

d total. Represents the total of aa+bb+cc, or the same d.

a total. Represents the total of dd+ee+ff, or the same as a.

vv total. Represents the total of gg+hh+ii, or the vertical height of the retainer at the level of the lateral incisors on the labial.

ww total. Represents the total of jj+kk+ll, or the vertical labial height of the retainer at the level of the canine.

xx total. Represents the total of mm+nn+oo, or the vertical buccal height of the retainer at the level of the first bicuspid.

yy total. Represents the total of pp+qq+rr, or the vertical buccal height of the retainer at the level of the second bicuspid.

zz total, Represents the total of ss+tt+uu, or the vertical buccal height of the retainer at the level of the first permanent molar, or same as c.

Table II
Dimensions Of The Deciduous 2nd Molars And Arch Widths Of Position Of 1st Permanent Molars For Occlus-O-Guide

| Size Occlus-o-Guide | Upper 2nd Dec. Molar Mesio-Distal Dimension mm. | Lower 2nd Dec. Molar Mesio-Distal Dimension mm. | Arch-Width Between Mesio-Buccal Cusps of Upper 1st Perm.Molars mm. | Arch-Width of Lower 1st Perm. Molars mm. | Free-Way Space |
|---|---|---|---|---|---|
| 1 G | 7.76 | 8.48 | 47.0 | 42.7 | 2.7 |
| 1½ G | 7.94 | 8.68 | 47.9 | 43.5 | 2.8 |
| 2 G | 8.13 | 8.88 | 48.8 | 44.3 | 2.9 |
| 2½ G | 8.31 | 9.08 | 49.6 | 45.0 | 3.0 |
| 3 G | 8.49 | 9.28 | 50.5 | 45.8 | 3.1 |
| 3½ G | 8.68 | 9.48 | 51.4 | 46.7 | 3.2 |
| 4 G | 8.86 | 9.68 | 52.3 | 47.5 | 3.3 |
| 4½ G | 9.04 | 9.88 | 53.2 | 48.3 | 3.4 |
| 5 G | 9.23 | 10.08 | 54.0 | 49.0 | 3.5 |
| 5½ G | 9.41 | 10.28 | 54.9 | 49.8 | 3.6 |
| 6 G | 9.59 | 10.48 | 55.8 | 50.6 | 3.7 |

Table III
Occlus-O-Guide
Distances From Incisal Edges To Gingival Margins

| Size | Lower Central Incisors mm. | Lower Lateral Incisors mm. | Lower Canines mm. | Upper Central Incisors mm. | Upper Lateral Incisors mm. | Upper Canines mm. |
|---|---|---|---|---|---|---|
| 1 | 3.8 | 3.1 | 5.1 | 5.5 | 4.7 | 4.7 |
| 1½ | 4.1 | 3.4 | 5.2 | 5.8 | 4.8 | 4.9 |
| 2 | 4.4 | 3.7 | 5.4 | 6.1 | 4.9 | 5.1 |
| 2½ | 4.7 | 4.0 | 5.5 | 6.4 | 5.0 | 5.3 |
| 3 | 5.0 | 4.3 | 5.7 | 6.7 | 5.1 | 5.5 |
| 3½ | 5.3 | 4.6 | 5.8 | 7.0 | 5.2 | 5.7 |
| 4 | 5.6 | 4.9 | 6.0 | 7.3 | 5.3 | 5.9 |
| 4½ | 5.9 | 5.2 | 6.1 | 7.6 | 5.4 | 6.1 |
| 5 | 6.2 | 5.5 | 6.3 | 7.9 | 5.5 | 6.3 |
| 5½ | 6.5 | 5.8 | 6.4 | 8.2 | 5.6 | 6.5 |
| 6 | 6.8 | 6.1 | 6.6 | 8.5 | 5.7 | 6.7 |

The orthodontists would utilize the positioner of the present invention in accordance with the following procedure. He would take a measurement of the area that would be occupied by the upper four incisor teeth and a proper size non-extraction preformed positioner is selected. If a conventional preformed positioner is used, the gingival tissues must be trimmed back, as described above so that the positioner does not abrade the widely outwardly tapering gingival areas 60. Alternatively, if the positioners are provided already trimmed back a proper amount, for example, as in Table I, the orthodontist would use said measurement to select the proper size pre-trimmed positioner. Normally the positioner would then be worn for approximately 3 to 4 hours a day with exercising (clenching and holding the teeth in the clenched position) and at night during sleep. When the overbite is corrected, the daytime wear can be cut down to one hour per day and at night. The positioner should then preferably be used until all of the permanent bicuspid and canine teeth have fully erupted.

Although the invention has been described in considerable detail with respect to a preferred embodiment thereof, it will be apparent that the invention is capable of numerous modifications and variations apparent to those skilled in the art without departing from the spirit and scope of the invention.

I claim:

1. A method of positioning teeth comprising the steps of:

providing an orthodontic positioner of the type which is generally U-shaped in plan view and includes in at least one of the top or bottom thereof a tooth receiving trough for receiving and positioning teeth, said providing step comprising selecting a preformed positioner having in the trough or troughs therein at least depressions of a size and shape for a subject patient having permanent incisor teeth, permanent canine teeth and permanent first bicuspid teeth and having a dimension across the front of the depressions of the incisor teeth equal to the dimensions across the front incisor teeth of the subject patient, applying the positioner for use by a patient at a mixed dentition stage of development wherein the patient has permanent incisors and permanent first molars, and wherein the deciduous canine and at least the first deciduous molars are absent and have not yet been replaced by the corresponding permanent canine and bicuspid teeth by applying the said selected preformed positioner to the patient's teeth, such use continuing for at least a portion of the time from the initial application of the positioner to the time that said permanent canine and bicuspid teeth have fully erupted, whereby such use causes early depression of the incisor teeth while permitting unhindered eruption of the said permanent canine and bicuspid teeth.

2. The method of claim 1, wherein said providing step includes providing a positioner having tooth receiving troughs in both the top and bottom thereof.

3. The method of claim 1, said applying step comprising applying the positioner for use until the permanent canine and bicuspid teeth are fully erupted.

4. The method of claim 1, wherein said selecting step includes selecting a positioner designed for a person having all permanent teeth from the first permanent molars, anteriorly thereof, and trimming back the gingival marginal edges of the labial-buccal flange thereof to a distance to prevent said margins from abrading the labial-buccal gum surfaces.

5. The method of claim 4, said trimming back including trimming back at least 50 percent of the part of the labial-buccal margin from the gum line to the outer gingival margin thereof.

6. The method of claim 5, said trimming back including trimming back to at least 70 percent of the part of the margin from the gum line to the outer gingival edge thereof adjacent the depressions for the first permanent molar.

7. The method of claim 5, said trimming back including eliminating part of the positioner containing the depressions for the second permanent molars.

8. The method of claim 1, said providing step further comprising measuring selected dimensions of the patient's mouth and based on such measurements selecting a preformed positioner having gingival margins previously trimmed back to avoid abrading the labial-buccal gum surfaces.

9. The method of claim 8, wherein said selecting step includes selecting a positioner from the set as described in Table I.

10. The method of claim 1, said providing step including selecting a preformed positioner having in the trough or troughs thereof depressions of a size and shape for a person having permanent teeth from the first permanent molar and anteriorly thereof except for the second deciduous molars which are present rather than the second permanent bicuspids, and said applying step including applying the positioner to a patient having second deciduous molars in place and only the first deciduous molars out and unreplaced.

11. The method of claim 10, wherein the selecting step includes selecting a positioner from the set as described in Table I, as modified by Table ble II.

12. The method of claim 10, wherein said providing step includes providing a positioner having tooth receiving troughs in both the top and bottom thereof.

13. The method of claim 10, said applying step comprising applying the positioner for use until the permanent canine and bicuspid teeth are fully erupted.

14. The method of claim 10, said providing step further comprising measuring selected dimensions of the patient's mouth and based on such measurements selecting a preformed positioner having gingival margins previously trimmed back to avoid abrading the labial-buccal gum surfaces.

15. An orthodontic positioner of the type which is generally U-shaped in plan view and includes a tooth receiving trough in at least one of the upper or lower sides thereof, which trough includes tooth receiving depressions for receiving and positioning teeth, said positioner including depressions for at least the permanent incisors, permanent cuspids, at least the first permanent bicuspids and the permanent first molar teeth of a given person, and wherein the gingival margins of the labial-buccal flange of the positioner are trimmed back relative to the labial-buccal flange of a positioner designed for a said given person having all permanent teeth from the firt permanent molars and anteriorly thereof to at least 50 percent of the original distance from the gingival edge of the gum line, so as not to abrade the labial-buccal gum surfaces of a patient having permanent incisors and a permanent first molar of the same size as said given person but also having lost, unreplaced deciduous canine and at least the first deciduous molars.

16. An orthodontic positioner according to claim 15, said positioner extending posteriorly only to the first permanent molar.

17. An orthodontic positioner according to claim 15, wherein the gingival margins are trimmed back to at least 70 percent of the original distance from the gum line to the gingival margin in the vicinity of the posterior teeth.

18. An orthodontic positioner according to claim 15, having dimensions as set forth in Table I.

19. A set of orthodontic positioners, each constructed according to claim 15, and having dimensions as set forth in Table I.

20. An orthodontic positioner according to claim 15, said positioner having depressions for all permanent teeth from the first permanent molars inclusive, anteriorly thereof.

21. An orthodontic positioner according to claim 20, said positioner extending posteriorly only to the first permanent molar.

22. An orthodontic positioner according to claim 15, said positioner having depressions for all permanent teeth from the first permanent molars anteriorly thereof except for the location of the permanent second bicuspids at which there is provided instead depressions for the second deciduous molars.

23. An othodontic positioner according to claim 23, said positioner being free of interproximal projections between the adjacent recesses for the first permanent molar and the second deciduous molar.

24. An orthodontic positioner according to claim 23, including a set of positioners dimensioned as set forth in Table I, as modified by Table II.

25. An orthodontic positioner according to claim 23, said positioner extending posteriorly only to the first permanent molar.

26. An orthodontic positioner according to claim 23, wherein said gingival margins are trimmed back to at least 50 percent of the orginal distance from the gingival edge to the gum line.

27. An orthodontic positioner according to claim 15, said positioner having tooth receiving troughs in both the top and the bottom thereof.

28. An orthodontic positioner of the type which is generally U-shaped in plan view and includes a tooth receiving trough in at least one of the upper or lower sides thereof, which trough includes tooth receiving depressions for receiving and positioning teeth, said positioner including depressions for at least the permanent incisors, permanent cuspids, at least the first permanent bicuspids and the permanent first molar teeth of a given person, and wherein the labial-buccal flange of the positioner extends no farther than the vicinity of the gingival edges of the tooth receiving depressions, so as to preclude abrading the labial-buccal gum surfaces of a patient having permanent incisors and a permanent first molar of the same size as said given person but also having lost, unreplaced deciduous canine and at least the first deciduous molars.

29. An orthodontic positioner according to claim 28, including both upper and lower troughs.

30. An orthodontic positioner according to claim 28, including only an upper trough.

31. A set of orthodontic positioners, each constructed according to claim 28, the positioners of the set having dimensions as set forth in Table I.

32. A set of orthodontic positioners, each constructed according to claim 28, the positioners of the set dimensioned as set forth in Table I, as modified by Tables II and III.

33. An orthodontic positioner according to claim 28, said positioner having depressions for all permanent teeth from the first permanent molars inclusive, anteriorly thereof.

34. An orthodontic positioner according to claim 33, said positioner extending posteriorly only to the first permanent molar.

35. An orthodontic positioner according to claim 28, said positioner having depressions for all permanent teeth from the first permanent molars anteriorly thereof except for the location of the permanent second bicuspids at which there is provided instead depressions for the second deciduous molars.

36. An orthodontic positioner according to claim 35, said positioner being free of interproximal projections between the adjacent recesses for the first permanent molar and the second deciduous molar.

* * * * *